United States Patent
Philip et al.

(10) Patent No.: US 10,737,848 B2
(45) Date of Patent: Aug. 11, 2020

(54) ONE PIECE CONTAINER AND LID

(71) Applicant: Amcor Rigid Packaging USA, LLC, Ann Arbor, MI (US)

(72) Inventors: Bradley S. Philip, Tecumseh, MI (US); Luke A. Mast, Brooklyn, MI (US); James Mierzwiak, Manchester, MI (US)

(73) Assignee: AMCOR RIGID PACKAGING USA, LLC, Ann Arbor, MI (US)

( * ) Notice: Subject to any disclaimer, the term of this patent is extended or adjusted under 35 U.S.C. 154(b) by 0 days.

(21) Appl. No.: 15/736,872

(22) PCT Filed: Jun. 16, 2015

(86) PCT No.: PCT/US2015/036004
§ 371 (c)(1),
(2) Date: Dec. 15, 2017

(87) PCT Pub. No.: WO2016/204731
PCT Pub. Date: Dec. 22, 2016

(65) Prior Publication Data
US 2018/0362224 A1    Dec. 20, 2018

(51) Int. Cl.
*B65D 43/16* (2006.01)
*B65D 81/26* (2006.01)
(Continued)

(52) U.S. Cl.
CPC .......... *B65D 43/162* (2013.01); *B65D 51/30* (2013.01); *B65D 81/266* (2013.01);
(Continued)

(58) Field of Classification Search
CPC .......... B65D 43/00–162; B65D 81/266; B65D 51/30; B65D 2543/00842;
(Continued)

(56) References Cited

U.S. PATENT DOCUMENTS

| | | | | |
|---|---|---|---|---|
| 1,692,189 A | * | 11/1928 | Scofield | B65D 41/12 215/327 |
| 3,039,482 A | * | 6/1962 | Goldberg | F16K 13/04 137/68.27 |
| 8,006,368 B2 | * | 8/2011 | Logel | B29C 45/006 264/250 |
| 8,783,485 B2 | * | 7/2014 | Logel | B65D 43/162 215/320 |

(Continued)

FOREIGN PATENT DOCUMENTS

JP        2010173674 A        8/2010

OTHER PUBLICATIONS

International Search Report and Written Opinion for PCT/US2015/036004, dated Mar. 9, 2016; ISA/KR.

*Primary Examiner* — Kareen K Thomas
(74) *Attorney, Agent, or Firm* — Harness, Dickey & Pierce, P.L.C.

(57) ABSTRACT

A one piece container including a body defining a receptacle and a lid connected to the body with a hinge. The lid includes a flange extending from an inner surface of the lid. The lid is movable between an open position thereby permitting access to the receptacle, and a closed position thereby restricting access to the receptacle. In the closed position, the flange of the lid extends into the receptacle to form a seal between a curved outer surface of the flange and a smooth inner surface of the body. The one piece container is formed as a single unit and may include a desiccant in the body or lid.

24 Claims, 3 Drawing Sheets

(51) Int. Cl.
*B65D 51/30* (2006.01)
*G01N 33/487* (2006.01)

(52) U.S. Cl.
CPC . *G01N 33/48778* (2013.01); *B65D 2251/105* (2013.01); *B65D 2543/00092* (2013.01); *B65D 2543/00351* (2013.01); *B65D 2543/00629* (2013.01); *B65D 2543/00842* (2013.01)

(58) Field of Classification Search
CPC ........... B65D 2543/00629; B65D 2543/00092; B65D 2543/00351; B65D 2251/105; G01N 33/00–48778
USPC ....... 220/810, 836, 837, 839, 840, 841, 842, 220/843, 263, 283, 359.2, 270, 269
See application file for complete search history.

(56) References Cited

U.S. PATENT DOCUMENTS

| | | | |
|---|---|---|---|
| 8,875,917 B2* | 11/2014 | Lourenco | B65D 47/0809 |
| | | | 215/231 |
| 8,960,491 B2* | 2/2015 | Logel | B65D 43/169 |
| | | | 215/235 |
| 9,428,311 B2* | 8/2016 | Bois | B65D 43/169 |
| 10,065,772 B2* | 9/2018 | Schneider | B65D 43/0212 |
| 10,246,241 B2* | 4/2019 | Logel | B65D 81/265 |
| 2007/0084735 A1* | 4/2007 | Lancesseur | B65D 51/30 |
| | | | 206/204 |
| 2010/0140116 A1 | 6/2010 | Stiene et al. | |
| 2011/0000930 A1* | 1/2011 | Logel | B65D 43/162 |
| | | | 220/849 |
| 2011/0210021 A1 | 9/2011 | Logel et al. | |

* cited by examiner

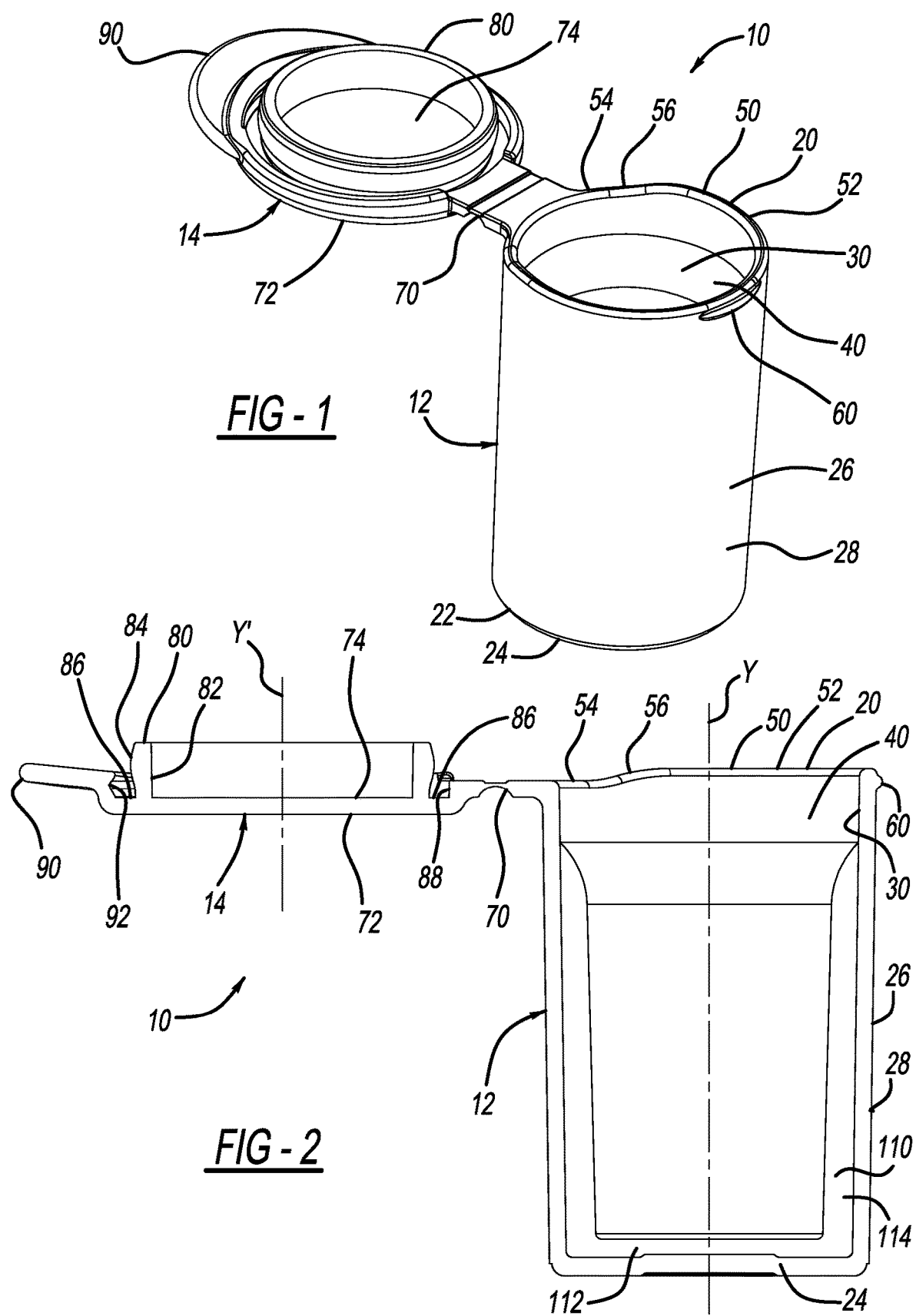

ONE PIECE CONTAINER AND LID

CROSS REFERENCE TO RELATED APPLICATION

This application is a U.S. National Phase Application under 35 U.S.C. 371 of International Application No. PCT/US2015/036004 filed on Jun. 16, 2015 and published as WO 2016/204731 A1 on Dec. 22, 2016. The entire disclosure of the above application is incorporated herein by reference.

FIELD

The present disclosure relates to a one piece container including a container body and integrated lid.

BACKGROUND

This section provides background information related to the present disclosure, which is not necessarily prior art.

While current containers are suitable for their intended use, they are subject to improvement. For example, a one piece container suitable for storing test strips for determining blood glucose and including at least the following features would be desirable: an improved seal between a body of the container and a lid; and an improved ability to keep contents of the container dry.

SUMMARY

This section provides a general summary of the disclosure, and is not a comprehensive disclosure of its full scope or all of its features.

The present teachings provide for a one piece container including a body defining a receptacle and a lid connected to the body with a hinge. The lid includes a flange extending from an inner surface of the lid. The lid is movable between an open position thereby permitting access to the receptacle, and a closed position thereby restricting access to the receptacle. In the closed position, the flange of the lid extends into the receptacle to form a seal between an outer surface of the flange and an inner surface of the body. The one piece container is formed as a single unit.

The present teachings further provide for a one piece container including a body defining a receptacle, a lid connected to the body with a living hinge, and an annular flange of the lid extending from an inner surface of the lid. The annular flange includes an inner surface and an outer surface opposite to the inner surface. The outer surface is curved along a length of the outer surface. The lid is movable between an open position thereby permitting access to the receptacle, and a closed position thereby restricting access to the receptacle. In the closed position the flange of the lid extends into the receptacle and the curved outer surface contacts an inner surface of the body to form a seal therebetween. The one piece container is injection molded as a single unit.

The present teachings also provide for a one piece container including a body with a rimless first end and a second end opposite to the rimless first end. The rimless first end defines an opening to a receptacle defined by the body. The rimless first end includes a first portion, a second portion, and a sloped portion extending between the first and second portions. The second portion is closer to a base of the container as compared to the first portion. A localized snap bead extends outward from the body and is spaced apart from the rimless first end of the body. A lid is connected to the body with a living hinge extending from the second portion of the rimless first end of the body. The living hinge is arranged 180° relative to the localized snap bead. An annular flange of the lid extends from an inner surface of the lid. The annular flange includes an inner surface and an outer surface opposite to the inner surface of the annular flange. The outer surface is curved along a length of the outer surface. A tab extends from the lid. The tab is arranged 180° relative to the living hinge and extends in a plane nonorthogonal to a longitudinal axis of the annular flange. The lid is movable between an open position thereby permitting access to the receptacle, and a closed position thereby restricting access to the receptacle. In the closed position the flange of the lid extends into the receptacle and the curved outer surface contacts an inner surface of the body to form a seal therebetween. The one piece container is injection molded as a single unit.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of a container according to the present teachings;

FIG. 2 is a cross-sectional view of the container of FIG. 1;

Corresponding reference numerals indicate corresponding parts throughout the several views of the drawings.

DETAILED DESCRIPTION

Figure 3:
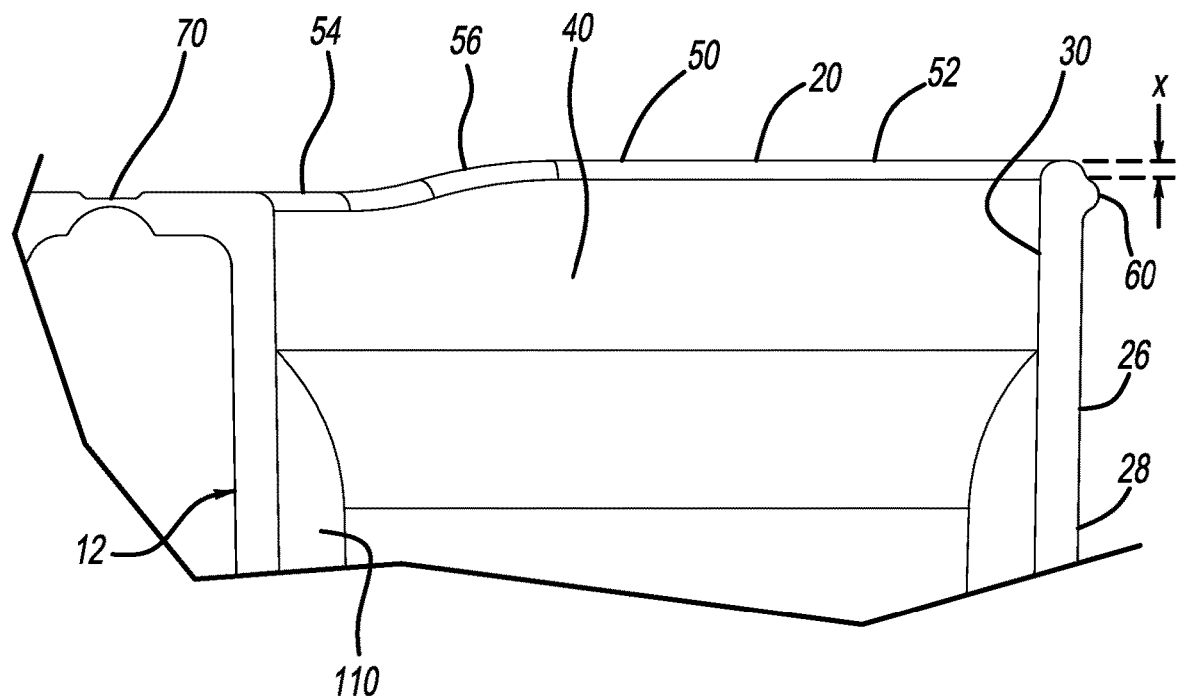
FIG. 3 is a cross-sectional view of an upper portion of a body of the container of FIG. 1.

Example embodiments will now be described more fully with reference to the accompanying drawings.

With initial reference to FIGS. 1 and 2, a one piece container according to the present teachings is generally illustrated at reference numeral 10. The container 10 generally includes a body 12 and a lid 14. The container 10 can be made of any suitable material, such as polyethylene terephthalate (PET), low-density polyethylene (LDPE), high-density polyethylene (HDPE), or polypropylene (PP), for example. The container 10 can be formed in any suitable manner such that the lid 14 is formed integral with the body 12. For example, the container 10 can be formed using any suitable injection molding process. The container 10 can be configured in any suitable manner to keep contents thereof dry. Thus, the container 10 can include any suitable desiccant, as described herein. The container 10 can be configured to hold test strips for determining blood glucose, for example.

Figure 5:
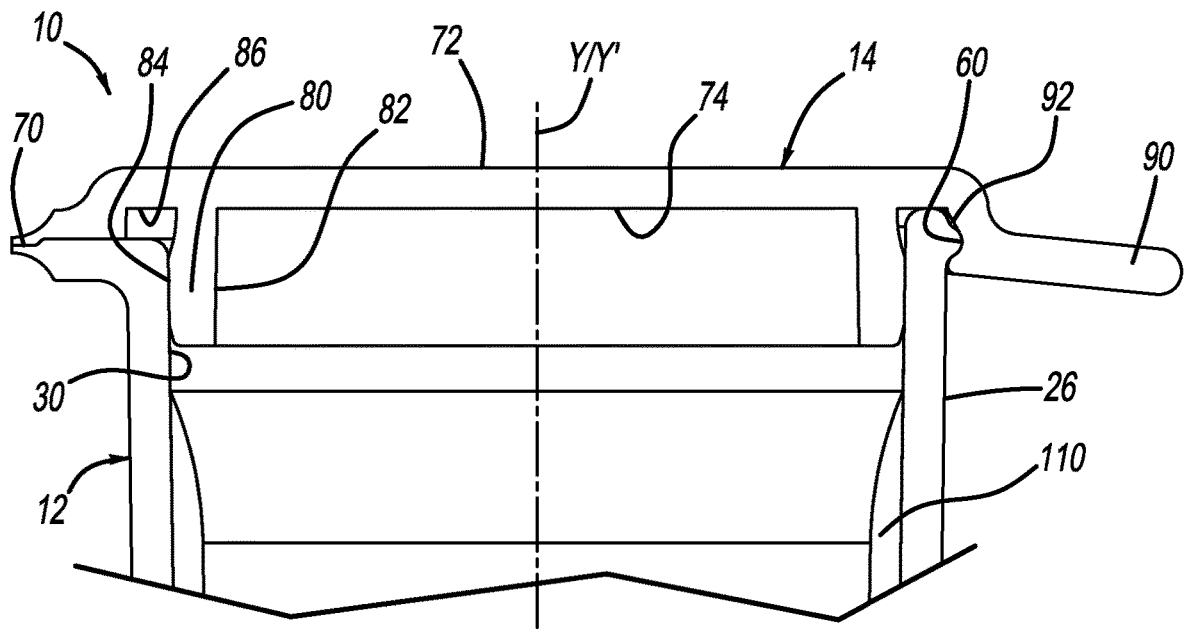
FIG. 5 is a cross-sectional view of the container of FIG. 1 with the lid of the container in a closed position.

The body 12 generally includes an upper end 20 and a lower end 22 opposite thereto. At the lower end 22 is a base 24, which can be generally circular. Extending from the base 24 is a sidewall 26, which can be any suitable shape, such as cylindrical or annular. The sidewall 26 includes an outer surface 28 and an inner surface 30 opposite thereto, which is generally smooth. The body 12 defines an internal volume 40, which generally provides a receptacle for contents of the container 10, such as blood glucose test strips. Specifically, the base 24 and the inner surface 30 of the cylindrical sidewall 26 define the internal volume 40. When the lid 14 is closed, as illustrated in FIG. 5, the lid 14 further defines the internal volume 40.

With continued reference to FIGS. 1 and 2, and additional reference to FIG. 3 for example, at the upper end 20 of the container 10 is an upper surface 50, which is rimless and generally defines an opening of the internal volume 40 when the lid 14 is in the open position of FIGS. 1-3, for example. The upper surface 50 includes a first portion 52, a second portion 54, and a sloped portion 56, which is between the first and second portions 52 and 54. The first portion 52 is higher than the second portion 54 such that the first portion 52 is further from the base 24 than the second portion 54. The first portion 52 and the second portion 54 are in spaced apart planes, each of which extend parallel to one another, as well as orthogonal to a longitudinal axis Y of the body 12. The lid 14 is connected to the body 12 at the second portion 54 by way of a hinge 70, which as described herein can be a living hinge.

The body 12 further includes a localized projection or snap bead 60, which protrudes from the outer surface 28 of the sidewall 26. The projection 60 does not extend entirely about the outer surface 28, but is rather confined to an area of the outer surface 28 that is opposite to, or 180° from, the hinge 70. The projection 60 does not extend from the upper surface 50, but is rather spaced apart from the upper surface 50 and the upper end 20 towards the lower end 22, as illustrated in FIG. 3 for example. The projection 60 may be spaced apart from the upper surface 50 and the upper end 20 by any suitable distance, such as a distance X, as illustrated in FIG. 3. The distance X can be any suitable distance.

The hinge 70 connecting the lid 14 to the body 12 can be any suitable hinge, such as a living hinge. The hinge 70 is integrally formed (such as integrally molded) with both the body 12 and the lid 14. Therefore, the container 10 is provided as a one piece container in which the body 12, the lid 14, and the living hinge 70 are integral and monolithic.

Figure 4:
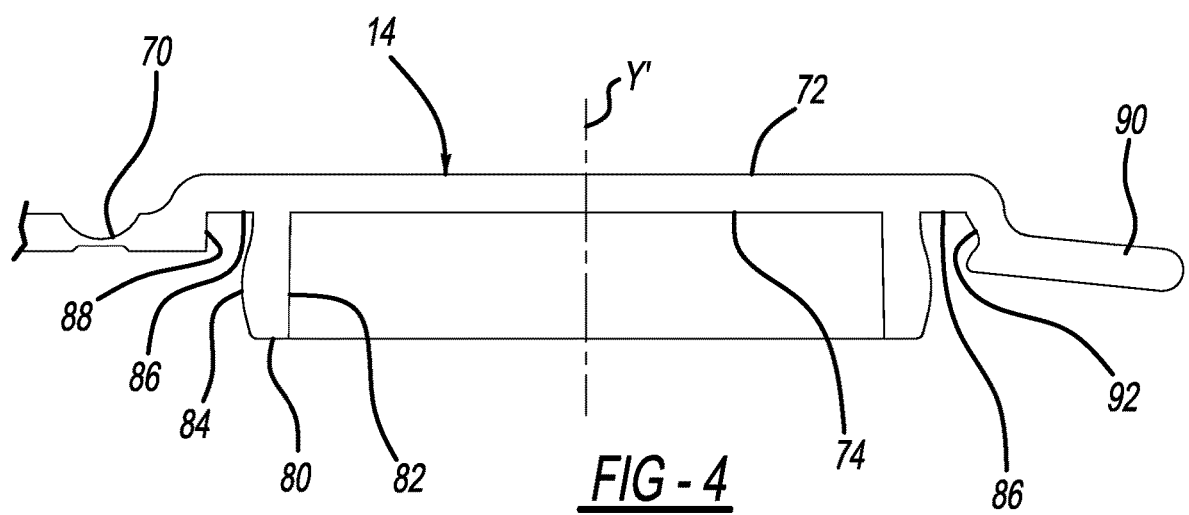
FIG. 4 is a cross-sectional view of a lid of the container of FIG. 1.

With continued reference to FIGS. 1 and 2, and additional reference to FIG. 4, the lid 14 includes an outer surface 72 and an inner surface 74, which is opposite to the outer surface 72. Extending from the inner surface 74 is an annular flange 80. The annular flange 80 is sized and shaped to be received within the body 12 at the upper end 20 such that the annular flange 80 extends past the upper surface 50 and into the internal volume 40 when the lid 14 is closed. A longitudinal axis Y' extends through an axial center of the annular flange 80. The annular flange 80 includes an inner flange surface 82, which is opposite to an outer flange surface 84. The inner flange surface 82 extends generally linearly from the inner surface 74 at generally a right angle relative to the inner surface 74. The outer flange surface 84 is curved along its length. For example, the outer flange surface 84 can be continuously curved along its length and can be shaped to have any suitable curve radius to provide a seal between the outer flange surface 84 and the inner surface 30 of the cylindrical sidewall 26 when the lid 14 is closed. The outer flange surface 84 may have a larger diameter than the inner surface 30 to form an interference fit. The inner wall of surface 30 may be smooth. The seal can be any suitable hermetic seal, such as an air, vapor, moisture, or liquid, seal extending continuously about the outer flange surface 84 in cooperation with inner wall 30.

The lid 14 further defines a lid receptacle 86. The lid receptacle 86 extends about at least a portion of the annular flange 80, and an inner portion of the lid receptacle 86 is defined by the outer flange surface 84. On a side of the lid receptacle 86 opposite to the outer flange surface 84 is an outer wall surface 88. A recess 92 is defined within the outer wall surface 88 at a portion thereof that is opposite to, and thus 180° from, the hinge 70. The recess 92 is configured to receive the projection 60 therein in order to help secure the lid 14 in the closed position, as explained further herein.

The lid 14 also includes a tab 90. The tab 90 extends outward from an area of the lid 14 that is opposite to, and thus 180° from, the hinge 70. The tab 90 does not extend about an entirety of the lid 14, but only the portion of the lid 14 opposite to the hinge 70. The tab 90 can be substantially horizontal such that it extends orthogonal to the longitudinal axis Y' of the lid 14, or the tab 90 can be angled such that it extends outward along a plane that is nonorthogonal to the longitudinal axis Y' of the lid 14. For example, in the closed position (FIG. 5) the tab 90 can be angled toward the lower end 22.

The container 10 can optionally include any suitable desiccant, such as desiccant 110 illustrated in FIGS. 2, 3, and 5. The desiccant 110 can be inserted within the body 12 as illustrated, and secured within the body 12 in any suitable manner. For example, the desiccant 110 can be molded to the inner surface 30 of the body 12. The desiccant 110 can also be an insert secured within the body 12 in any suitable manner, such as with a press fit or any suitable adhesive. The desiccant 110 generally includes a desiccant base 112 and a cylindrical sidewall 114 extending from the base 112. The desiccant base 112 is sized and shaped to be seated on the base 24 within the internal volume 40, and the sidewall 114 is sized and shaped to abut the inner surface 30 of the sidewall 26. The desiccant 110 does not extend entirely to the upper end 20 of the body 12, but instead terminates prior to reaching the upper end 20 in order to provide clearance for the annular flange 80 when the lid 14 is closed.

FIGS. 1 and 2 illustrate the lid 14 in the open position, in which the lid 14 does not obstruct access to the internal volume 40. With reference to FIG. 5, the lid 14 can be moved to the closed position in order to seal the internal volume 40. Specifically, the lid 14 is rotated about the living hinge 70 from the open position in order to position the annular flange 80 within the internal volume 40 at the upper end 20 and align the longitudinal axis Y' of the lid 14 with the longitudinal axis Y of the body 12. Because the second portion 54 of the upper surface 50 is lower than the first portion 52, the second portion 54 provides a clearance for the annular flange 80 as the lid 14 is rotated to the closed position.

In the closed position, the first portion 52 of the upper surface 50 and part of the sloped portion 56 adjacent to the first portion 52 are seated within the lid receptacle 86. The outer flange surface 84 of the annular flange 80 abuts the inner surface 30 of the cylindrical sidewall 26 to provide a seal between the outer flange surface 84 and the inner surface 30. The projection 60 is seated within the recess 92 of the lid 14 in order to secure the lid 14 in the closed position of FIG. 5. To open the lid 14, the tab 90 is lifted and flexed to pull the annular flange 80 out from within the internal volume 40 and move the lid 14 such that the projection 60 is no longer within the recess 92 of the lid 14.

Figure 6:
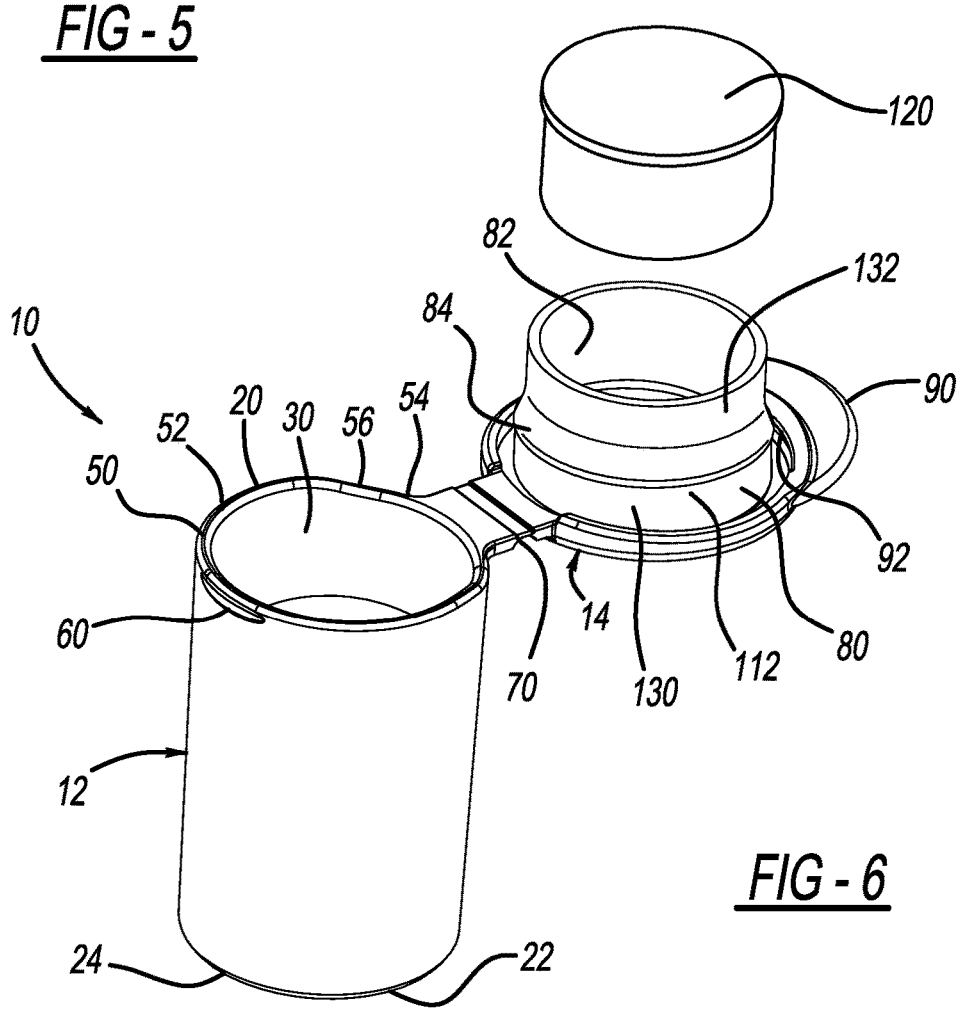
FIG. 6 is a perspective view of another container according to the present teachings including a lid configured to receive a desiccant therein.

With reference to FIG. 6, the lid 14 can include the desiccant, such as in the form of a desiccant insert 120. The desiccant insert 120 can be any suitable desiccant, such as a granular desiccant. To accommodate the desiccant insert 120, the annular flange 80 can include a first extended portion 130 and a second extended portion 132. The first extended portion 130 extends from the inner surface 74 of the lid 14 to the curved portion of the outer flange surface 84. The second extended portion 132 extends from the curved portion of the outer flange surface 84 on a side thereof opposite to the first extended portion 130. The second extended portion 132 can be tapered inward to help secure the desiccant insert 120 within the annular flange 80, and facilitate insertion of the second extended portion 132 within the internal volume 40 when the lid 14 is closed. The desiccant insert 120 can be retained in the annular flange 80 in any suitable manner, such as with a press fit, heat forming, heat staking, ultrasonic welding, bonding, or the like.

The description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used is for the purpose of describing particular example embodiments only and is not intended to be limiting. The singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors interpreted accordingly.

What is claimed is:

1. A one piece container comprising:
    a body defining a receptacle, the body includes an upper end, a base at a lower end opposite to the upper end, and a rimless upper surface at the upper end defining an opening of the receptacle, the rimless upper surface including a first portion, a second portion, and a sloped portion between the first and second portions, the first portion is further from the base than the second portion such that the first portion is higher than the second portion;
    a lid connected to the body with a living hinge that is integral with both the body and the lid, the lid including a flange extending from an inner surface of the lid;
    wherein:
        the lid is movable between an open position thereby permitting access to the receptacle, and a closed position thereby restricting access to the receptacle;
        in the closed position the flange of the lid extends into the receptacle to form a seal between an outer surface of the flange and an inner surface of the body; and
        the body, living hinge, and lid are injection molded together as a single, integral piece such that the one piece container is formed as a single unit.

2. The one piece container of claim 1, further comprising a desiccant at one of the body or the lid;
    wherein the desiccant is at least one of an insert or molded to the container.

3. The one piece container of claim 1, wherein first portion is in a first plane and the second portion is in a second plane, the first and second planes extend parallel to one another and perpendicular to a longitudinal axis of the body.

4. The one piece container of claim 1, further comprising:
a localized projection extending from an outer surface of the body opposite to the living hinge, the localized projection spaced apart from the upper end of the body and confined to an area of the body opposite to the living hinge; and
a recess defined in the lid configured to receive the localized projection therein when the lid is in the closed position to secure the lid in the closed position.

5. The one piece container of claim 1, wherein the lid includes a tab extending in a plane that is nonorthogonal to a longitudinal axis of the lid.

6. The one piece container of claim 1, wherein the lid includes a tab extending in a plane that is orthogonal to a longitudinal axis of the lid.

7. The one piece container of claim 1, wherein the flange includes an inner surface and an outer surface opposite to the inner surface, the outer surface is curved along its length, in the closed position the outer surface contacts the inner surface of the body to form the seal.

8. The one piece container of claim 1, wherein the lid defines a lid receptacle configured to receive the upper surface of the container therein.

9. The one piece container of claim 1, wherein the seal is hermetic.

10. The one piece container of claim 1, wherein the body has a smooth inner wall.

11. A one piece container comprising:
a body defining a receptacle, the body includes an upper end, a base at a lower end opposite to the upper end, and a rimless upper surface at the upper end defining an opening of the receptacle, the rimless upper surface including a first portion, a second portion, and a sloped portion between the first and second portions, the first portion is further from the base than the second portion such that the first portion is higher than the second portion;
a lid connected to the body with a living hinge that is integral with both the body and the lid; and
an annular flange of the lid extending from an inner surface of the lid, the annular flange including an inner surface and an outer surface opposite to the inner surface, the outer surface is curved along a length of the outer surface;
wherein:
the lid is movable between an open position thereby permitting access to the receptacle, and a closed position thereby restricting access to the receptacle;
in the closed position the flange of the lid extends into the receptacle and the curved outer surface contacts an inner surface of the body to form a seal therebetween; and
the body, living hinge, and lid are injection molded together as a single, integral piece such that the one piece container is formed injection molded as a single unit.

12. The one piece container of claim 11, further comprising a desiccant insert within the body.

13. The one piece container of claim 11, further comprising a desiccant molded within the body.

14. The one piece container of claim 11, further comprising a desiccant insert seated within the annular flange of the lid.

15. The one piece container of claim 11, further comprising:
a localized snap bead extending from an outer surface of the body opposite to the hinge, the localized snap bead spaced apart from an upper end of the body and confined to an area of the body opposite to the hinge;
a snap bead recess defined in the lid configured to receive the localized snap bead therein when the lid is in the closed position to secure the lid in the closed position; and
a lid receptacle configured to receive a portion of the upper surface of the body therein.

16. The one piece container of claim 11, further comprising a tab extending from the lid at a location 180° relative to the living hinge.

17. The one piece container of claim 11, wherein the seal is hermetic.

18. The one piece container of claim 11, wherein the body has a smooth inner wall.

19. A one piece container comprising:
a body including a rimless first end, a second end opposite to the rimless first end, and a sidewall extending between the rimless first end and the second end, the rimless first end defining an opening to a receptacle defined by the body, the rimless first end includes a first portion, a second portion, and a sloped portion extending between the first and second portions, the second portion is closer to a base of the container as compared to the first portion;
a localized snap bead extending outward from the body and spaced apart from the rimless first end of the body;
a lid connected to the body with a living hinge extending from the second portion of the rimless first end of the body, the living hinge arranged 180° relative to the localized snap bead, the living hinge is integral with both the body and the lid;
an annular flange of the lid extending from an inner surface of the lid, the annular flange including an inner surface and an outer surface opposite to the inner surface of the annular flange, the outer surface is curved along a length of the outer surface; and
a tab extending from the lid, the tab arranged 180° relative to the living hinge and extending in a plane nonorthogonal to a longitudinal axis of the annular flange;
wherein:
the lid is movable between an open position thereby permitting access to the receptacle, and a closed position thereby restricting access to the receptacle;
in the closed position the flange of the lid extends into the receptacle and the curved outer surface contacts an inner surface of the body to form a seal therebetween; and
the body, living hinge, and lid are injection molded together as a single, integral piece such that the one piece container is formed as a single unit.

20. The one piece container of claim 19, further comprising a desiccant insert within the body.

21. The one piece container of claim 19, further comprising a desiccant molded within the body.

22. The one piece container of claim 19, further comprising a desiccant insert seated within the annular flange of the lid.

23. The one piece container of claim 19, wherein the sidewall includes a smooth inner wall.

24. The one piece container of claim 19, wherein the seal is hermetic.

* * * * *